(12) United States Patent
Kimura

(10) Patent No.: US 7,074,225 B2
(45) Date of Patent: Jul. 11, 2006

(54) MEDICAL DRILLING MACHINE

(75) Inventor: Junichi Kimura, Saitama (JP)

(73) Assignee: Japan Universal Technologies, Inc., Tokyo (JP)

( * ) Notice: Subject to any disclaimer, the term of this patent is extended or adjusted under 35 U.S.C. 154(b) by 368 days.

(21) Appl. No.: 10/637,024

(22) Filed: Aug. 8, 2003

(65) Prior Publication Data

US 2004/0138667 A1   Jul. 15, 2004

(51) Int. Cl.
*A61B 17/16*  (2006.01)
*A61B 17/17*  (2006.01)

(52) U.S. Cl. .......................................... 606/80; 606/97
(58) Field of Classification Search ................ None
See application file for complete search history.

(56) References Cited

FOREIGN PATENT DOCUMENTS

| JP | 01-501207 A | 4/1989 |
|---|---|---|
| JP | 05-003882 A | 1/1993 |
| JP | 09-019437 A | 1/1997 |
| JP | 10-075960 A | 3/1998 |
| JP | 11-244300 A | 9/1999 |
| JP | 2002-224125 A1 | 8/2002 |

*Primary Examiner*—David H. Willse
*Assistant Examiner*—Genevieve A-L. Hill
(74) *Attorney, Agent, or Firm*—Rader, Fishman & Grauer PLLC

(57) ABSTRACT

To facilitate positioning of a drill bit and alleviate burden to a user, a medical drill machine including a drive shaft gripping a drill bit, a casing constituted of X-ray transparent material and capable of housing the drive shaft, and a force transferring mechanism for transferring rotational force to the drive shaft is provided. In this medical drill machine, a first guide and a second guide constituted of X-ray opaque material are fixed at given positions along an axial direction of the drive shaft in the casing. Both guides are arranged coaxially with the axis of the drive shaft, and are formed in mutually different shapes. A slant direction of the drill bit can be recognized from any relative misalignment of the mutually different shapes of the guides included in an X-ray image along the ideal axial line.

12 Claims, 12 Drawing Sheets

(A)

(B)

MEDICAL DRILLING MACHINE

BACKGROUND OF THE INVENTION

1. Field of the Invention

The present invention relates to a medical drilling machine with a drive shaft which is rotatably held and is housed in an X-ray transparent casing, and more particularly to a technique for achieving accurate boring operation.

2. Description of the Related Art

In surgical operation or the like, there are instances where a hole must be bored with a medical drilling machine at a position that is not directly observable inside the body of a patient. Typically, such holes are bored in bone or transplant materials transplanted into the body. When boring the holes at a position which is not directly observable, X-ray images must be used to position the drill bit accurately.

FIG. 12 shows a conventional medical drilling machine disclosed in Japanese Patent Laid-Open Publication No. Hei 9-19437.

This medical drilling machine 1 includes: a casing 11 made of X-ray transparent material; a drive shaft 16 housed inside the casing; and a pair of bevel gears 12, 13 for transferring rotational force to the drive shaft 16. One of the bevel gears 12 is coaxially arranged along the same axis as the drive shaft 16, and the other bevel gear 13 is provided at one end of an input shaft 15. The input shaft 15 is held in the casing 11 by a bearing 14. The drive shaft 16 and the bevel gears 12, 13 are also made of X-ray transparent material.

The drive shaft 16 is held rotatably by two similarly shaped bearings 17, 18 made of X-ray opaque materials. A chuck 20 is provided at one end of the drive shaft 16, and a drill bit 19 is gripped by the chuck 20.

Next, a simple explanation is given regarding a procedure using the medical drilling machine 1 to form a bolt hole in a bone of a human body.

Before using the medical drilling machine 1, first, a drive motor 21 is attached to the input shaft 15. Then, X-rays are radiated along the direction in which the bolt hole will be bored (hereinafter, referred to as the "ideal axial line R"). The doctor firmly clutches the medical drilling machine 1 in his or her arm, and when the drilling machine enters into an X-ray radiation field T, an image such as shown in FIG. 13 is obtained by the X-rays. An axial tip 19a of the drill bit 19, an end surface 18a of the bearing 18, and the human bone B appear in the X-ray image. Therefore, the bolt hole can be formed in the bone by making the drill bit 19 rotate as the medical drilling machine 1 is advanced forward in a straight direction.

However, it is difficult actually to form an ideal bolt hole. The reason for this is that when the drill bit 19 is advanced forward in the direction of the ideal axial line R, there inevitably occurs misalignment of the axial center, or slanting of the drill bit 19, or other similar problems, and prompt correction thereof was difficult.

In more specific terms, when the drill bit 19 slants with respect to the direction of the ideal axial line R, the axial centers of the two bearings 17, 18 become misaligned, causing an oval ring D to be included in the X-ray image as shown in FIG. 14.

When the doctor sees this image, the doctor understands that the drill bit 19 has slanted along a long axis D1 across the length of the oval ring D. However, there still is a problem in that the doctor can not judge which direction the drill bit 19 is slanting along the long axis D1. As a result, the doctor would adjust the direction of the drill bit 19 in the wrong direction, causing the drill hole C to slant even further, or requiring time to adjust the direction of the drill bit 19, thus creating a problem of lengthening the operation time.

Furthermore, since the drive motor 21 is provided as a separate unit from the medical drilling machine 1, there was a problem in that it was very difficult for the doctor to hold. With this structure it was fundamentally difficult to position the drill bit 19 accurately and/or maintain the position. As described above, drill hole errors occurred easily, even when observing the misalignment of the two bearings 17, 18 in X-ray images.

SUMMARY OF THE INVENTION

The present invention has been made to solve the above-mentioned problems, and it is therefore an object of this invention to provide a medical drilling machine that relieves burden to a user such as a doctor, while facilitating the boring of an accurate hole.

In order to achieve the above-mentioned objects, a medical drilling machine according to the present invention includes: a drive shaft held in place in a rotatable fashion, gripping a drill bit by means of a chuck provided to an end of the drive shaft; a casing constituted of X-ray transparent material, being capable of housing the drive shaft; and a force transfer mechanism for transferring rotational force to the drive shaft. In this medical drilling machine, a first guide and a second guide constituted of X-ray opaque material are fixed at given distances from each other along an axial direction of the drive shaft inside the casing; the first guide and the second guide are arranged coaxially along an axial center of the drive shaft and are formed in mutually different shapes; and X-rays are radiated along a direction of an ideal axial line traveled by the drill bit, such that a slant direction of the drill bit with respect to the ideal axial line can be observed from any relative misalignment of, and the mutually different shapes of, the first and the second guides.

The inventor of the present invention noticed that it is difficult to observe the accurate slant direction of the drill bit based only on whether outer shape of the two bearings depicted by X-rays matched up with each other or not, as was done in the conventional art. Therefore, the inventor provided the first and the second guides deliberately having the mutually different shapes.

According to this construction, by confirming the shape of the guides beforehand, the user can accurately read the slant direction of the drill bit from the relative misalignment between the first and the second guides. As a result, the slant of the drill bit can be corrected quickly, to enable formation of the drill hole substantially corresponding to direction of the ideal axial line. This also contributes to alleviation of burden (work) for the doctor or other user.

When the first and the second guides are configured having "mutually different shapes", this means simply that their respective shapes do not completely match each other, and it means that it is sufficient if the guides can be distinguished one from the other when their axial centers become relatively misaligned with each other. Even if they have mutually similar shapes simply formed in different sizes, this is included in the concept of having "mutually different shapes" provided the guides can be mutually distinguished. Additionally, the same is true for example in a case where the guides have similar designs (e.g., as equilateral triangles having sides of equal lengths) but arranged at mutually different phases (e.g., when the topmost angles of the triangles are phased 60° from each other).

Furthermore, the present invention also includes a case where the images of the guides overlap and the first guide and the second guide cannot be discerned one from the other when the axial centers of the guides are aligned with each other, but their mutually different shapes are emphasized when their axial centers become misaligned.

In the invention described above, when a portion of the casing is dedicated only for the first and the second guides, the structure of the casing becomes complicated and oversized, and the manufacturing costs increase. Therefore, in the above-mentioned case it is desirable that the drive shaft is held in a rotatable fashion by means of a first bearing and a second bearing constituted of X-ray transparent material, and predetermined housing portions are formed to non-rotating portions of the first and the second bearings; and X-ray opaque material is inserted into the housing portions of the first and the second bearings to provide the first guide in the first bearing, and provide the second guide in the second bearing.

The above-mentioned construction enables effective exploitation of the first and the second bearings, which are already arranged coaxially with the central axis for functional reasons, thus enabling the simple construction and reduction of manufacturing costs.

Additionally, similarly to the above-mentioned construction, it is desirable to form housing portions to the inner surfaces of the cylindrical portions for housing the first and the second bearings and to insert X-ray opaque material into the housing portions in order to provide the first guide to the first bearing, and provide the second guide to the second bearing.

In a further aspect of the above-mentioned invention, it is desirable that the casing is provided with a drive motor for making the drive shaft rotate via the force transfer mechanism, and a battery for the drive motor. According to this construction, the entire machine becomes a single unit and becomes easier to use, enabling accurate positioning of the drill bit. Therefore, since the above-mentioned first and second guides can be utilized effectively, the slant of the drill bit can be corrected smoothly using on the guides.

Furthermore, in yet another aspect of the above-mentioned invention, it is desirable that the drive motor is arranged to be displaced from the axial line of the drive shaft, and a motor shaft of the drive motor is arranged in parallel with the axial line, a grip portion is provided as an integral part of the casing, on an opposite side of the drive shaft from the side where the drive motor is located, and the battery is provided to a grip end side of the grip portion.

The doctor or other user typically holds the medical drilling machine at various angles. Therefore, by adopting the above-mentioned construction the battery, the grip portion, the drill bit (the drive shaft) and the drive motor are lined up one after the other such that the heavier battery and the drive motor are positioned at either end, and the grip portion and the drill bit which function as a fulcrum or point of support are arranged between the battery and the drive motor. Therefore, the balance properties of the device as a whole are excellent, and the drill bit can be positioned quickly by gripping the grip portion, in addition to alleviating the burden on the arm of the doctor or other user.

Similarly, in yet another aspect of the above-mentioned invention, it is desirable that the drive motor is arranged to be displaced from the axial line of the drive shaft, and a motor shaft of the drive motor is arranged in parallel with the axial line; a grip portion is provided as an integral part of the casing, on an opposite side of the drive motor from the side where the drive shaft is located; and the battery is provided to a grip end side of the grip portion.

Furthermore, in still another aspect of the above-mentioned invention, it is desirable that a drive shaft through-hole is provided along the axial line of the drive shaft, and a casing through-hole is provided to the casing along the line of extension of the drive shaft through-hole; and the back end of the drill bit held by the drive shaft can be housed into both the drive shaft through-hole and the casing through-hole.

By adopting the above-mentioned construction, a long drill bit can be used when boring a hole of considerable length along the axial direction into the bone.

DETAILED DESCRIPTION OF THE PREFERRED EMBODIMENTS

Hereinafter, an example of an embodiment of the present invention will be described in detail, with reference to the drawings.

Figure 1:
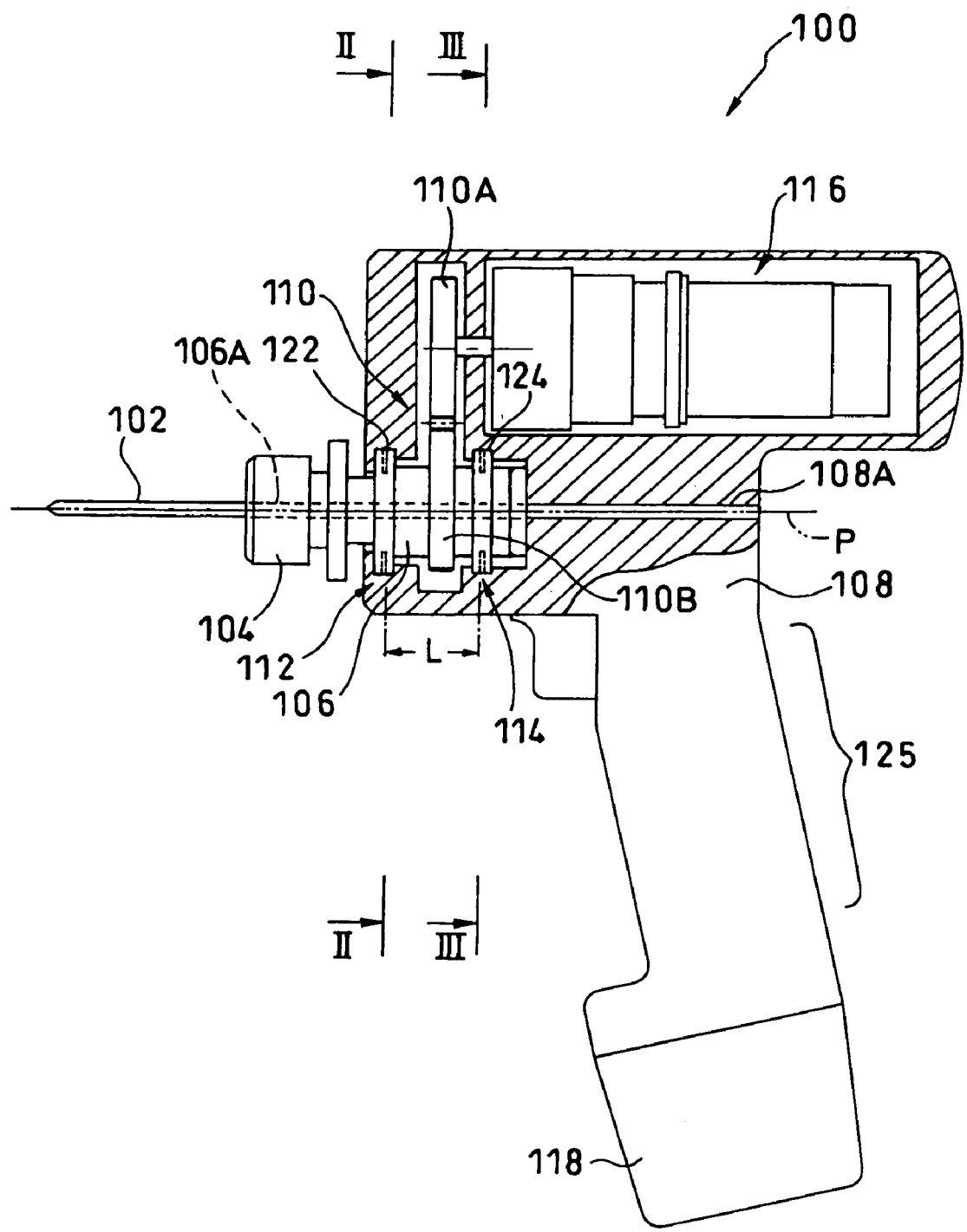
FIG. 1 is an overall constructional view showing a medical drilling machine according to an embodiment of the present invention.

FIG. 1 shows a medical drilling machine (hereinafter, "drill machine") 100, in accordance with a first embodiment of the present invention.

The drill machine 100 includes: a drill bit 102; a drive shaft 106 gripping the drill bit 102 by means of a chuck 104 provided at the end of the drive shaft; a casing 108 capable of housing the drive shaft 106; and a force transferring mechanism 110 for transferring rotational force to the drive shaft 106.

The drive shaft 106 is held rotatably by a first bearing 112 and a second bearing 114 provided inside the casing 108.

The drive shaft 106, both the bearings 112, 114, and the casing 108 are made of X-ray transparent material.

Note, however, that it is sufficient if only the part of the casing 108 around the drive shaft 106 is made of the X-ray transparent material. It is not necessary to make the entire casing 108 of the X-ray transparent material.

Furthermore, a drive motor 116 is housed in the casing 108. The force transferring mechanism 110 includes: a pinion 110A provided to a motor shaft of the drive motor 116; and a gear 110B which meshes with the pinion 110A and is provided integrally around the drive shaft 106. Therefore, the rotational force from the drive motor 116 is transferred through the pinion 110A and the gear 110B to the drive shaft 106.

A battery 118 for the drive motor 116 is also attached to the casing 108.

Figure 2:
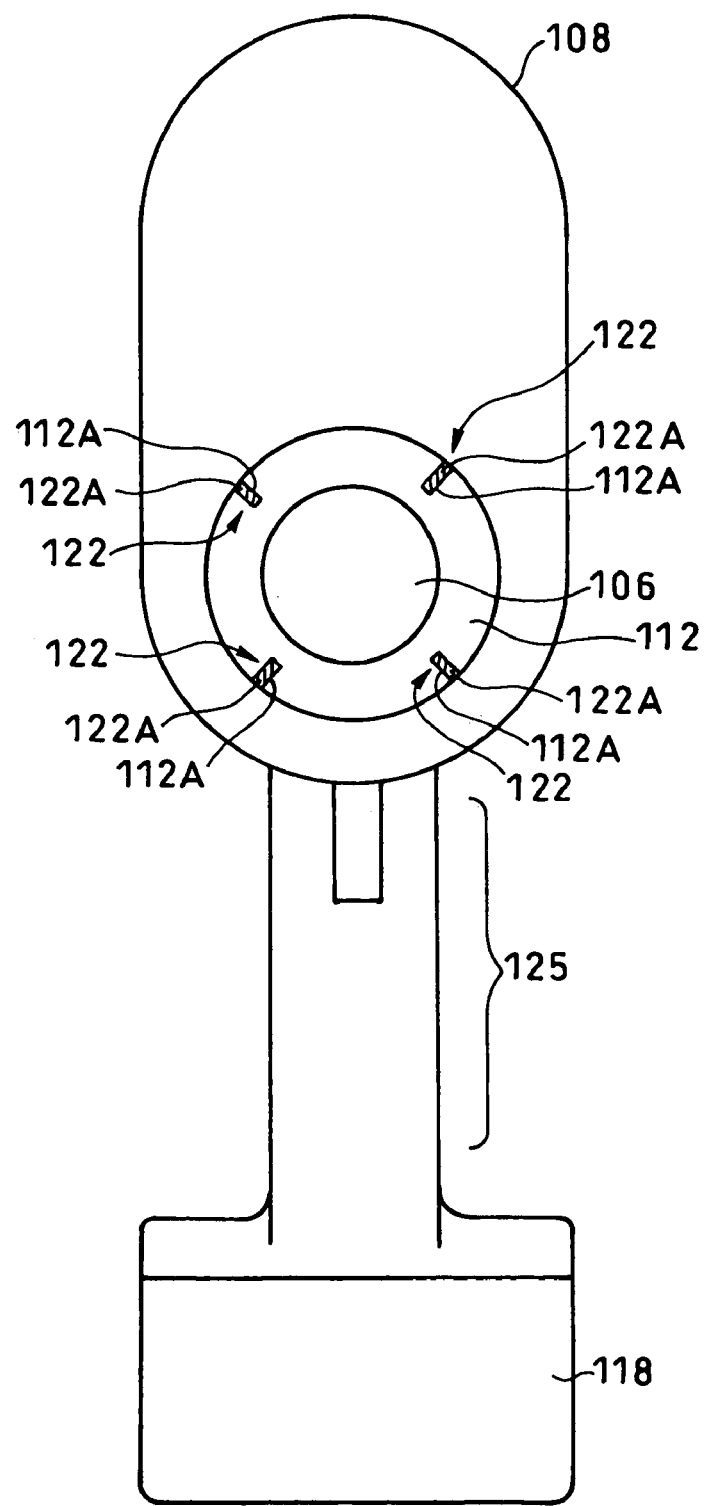
FIG. 2 is a cross-sectional view taken along the line II—II in FIG. 1.
Figure 3:
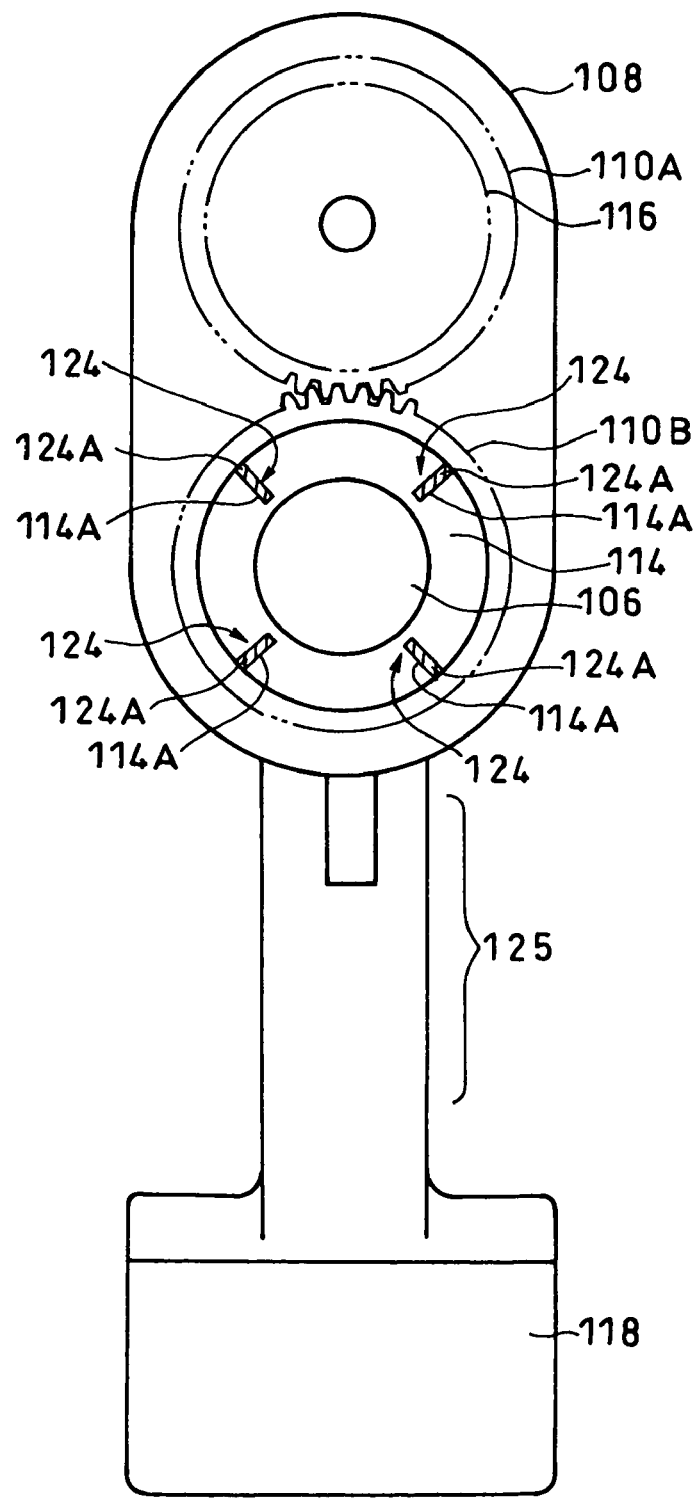
FIG. 3 is a cross-sectional view taken along the line III—III in FIG. 1.

The first and the second bearings 112, 114 are so-called "sliding bearings" shaped as sleeves, as can be seen close-up in FIG. 2 and FIG. 3. Housing portions 112A, 114A are provided to non-rotating portions of the first and the second bearings 112, 114 (however, in a "sliding bearing" the entire bearing is "non-rotating portion"). X-ray opaque materials 122A, 124A (i.e., in the present example metal rods are used) are inserted into each of the housing portions 112A, 114A. These X-ray opaque materials 122A, 124A constitute a first guide 122 in the first bearing 112, and a second guide 124 in the second bearing 114. Note, however, that if rolling bearings are used for the first and the second bearings, then only their outer rings affixed to the casing 108 will serve as the non-rotating portions.

More specifically, to form the housing portions 112A, 114A, holes are formed to the outer surfaces of the first and the second bearings 112, 114 at 90-degree intervals toward the radial center of the shaft. The length (depth) of these holes is such that the holes on the second bearing 114 side are longer (deeper) than those on the first bearing 112 side. The length of the above-mentioned X-ray opaque materials 122A, 124A are substantially the same length as the holes.

Returning to FIG. 1, the first guide 122 and the second guide 124 are fixed at positions to create a predetermined distance L between the first guide and the second guide, along the drive shaft 106 inside the casing 108. Further, the first guide 122 and the second guide 124 are positioned along the same axis as the drive axis 106, but are formed in mutually different shapes.

The drive motor 116 is arranged at a position displaced from an axial line P of the drive shaft 106, and its motor axis is arranged parallel to the axial line P. Further, a grip portion 125 formed by a portion of the casing 108 is provided on the opposite side of the drive shaft 106 from the drive motor 116 side. The battery 118 is removeably attached to a grip end side of the grip portion 125. The battery 118 is made removeable so that it can be exchanged for a new battery when the residual energy in the battery 118 is exhausted while performing operations. However, of course, the battery 118 may also be housed inside the casing 108.

A drive shaft through-hole 106A is formed to the drive shaft 106 along the axial line P, and a casing through-hole 108A is formed to the casing 108 along a linear extension from the above-mentioned drive shaft through-hole 106A (i.e., in alignment with the axial line P). As a result, the drill bit 102 held by the drive shaft 106 can extend through both the drive shaft through-hole 106A and the casing through-hole 108A.

Next, explanation is given regarding examples of operations and usage of the present drill machine 100.

Figure 4:
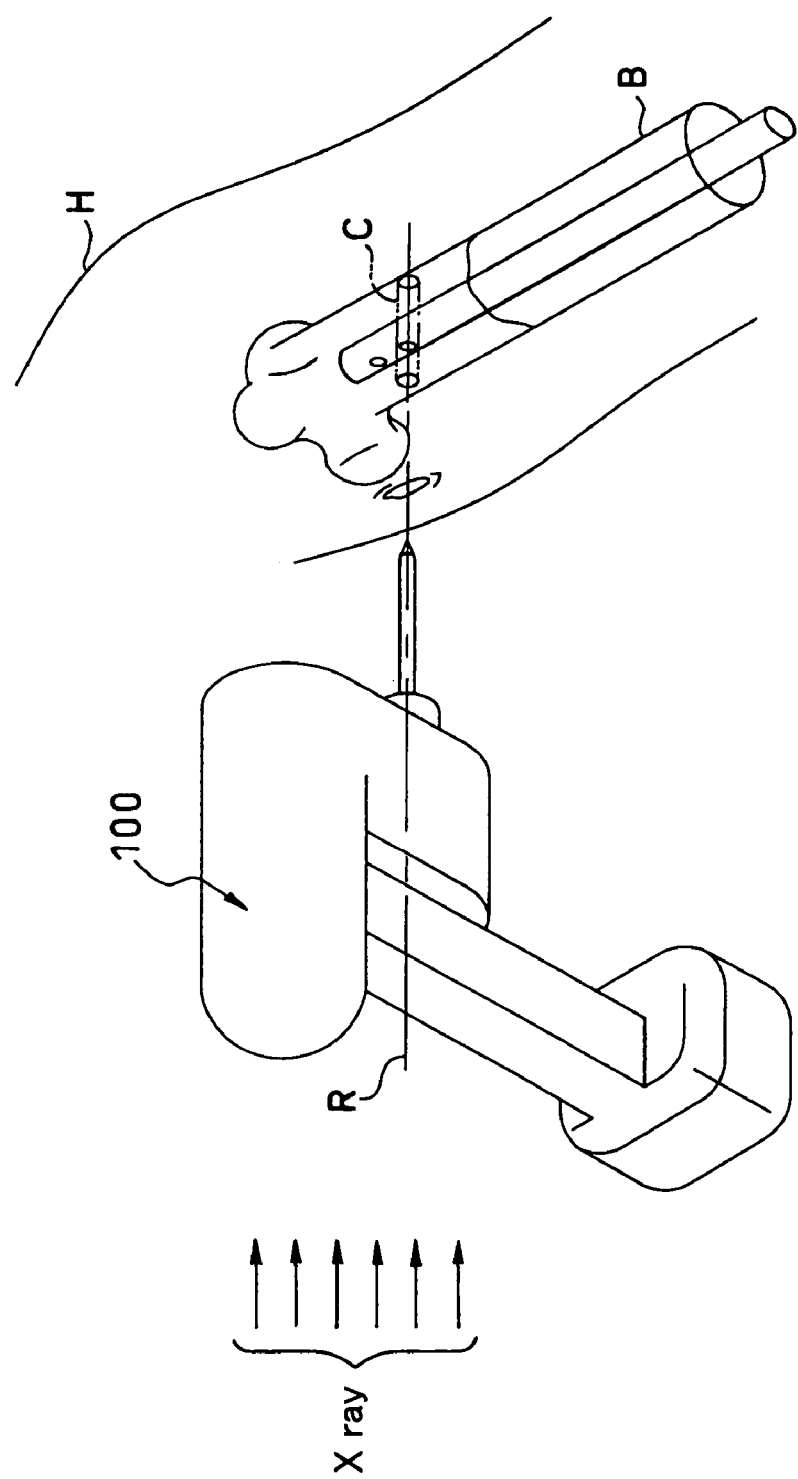
FIG. 4 is a perspective view of an example of the medical drilling machine as it is being used.

FIG. 4 shows formation of a bolt hole C into a bone B below the knee of a human body H. First, X-rays are radiated in the direction of an ideal axial line R along which the drill bit 102 is to be advanced. An image reception apparatus (not shown in the diagram) is arranged at a place above the human body H along the direction traveled by the X-rays. When the X-rays do not arrive at the other side, this produces shadows of the materials (members) X-rays cannot transmit through. Note that, the ideal axial line R mentioned above refers to the axial direction along which the doctor plans to form the bolt hole C.

Figure 5:
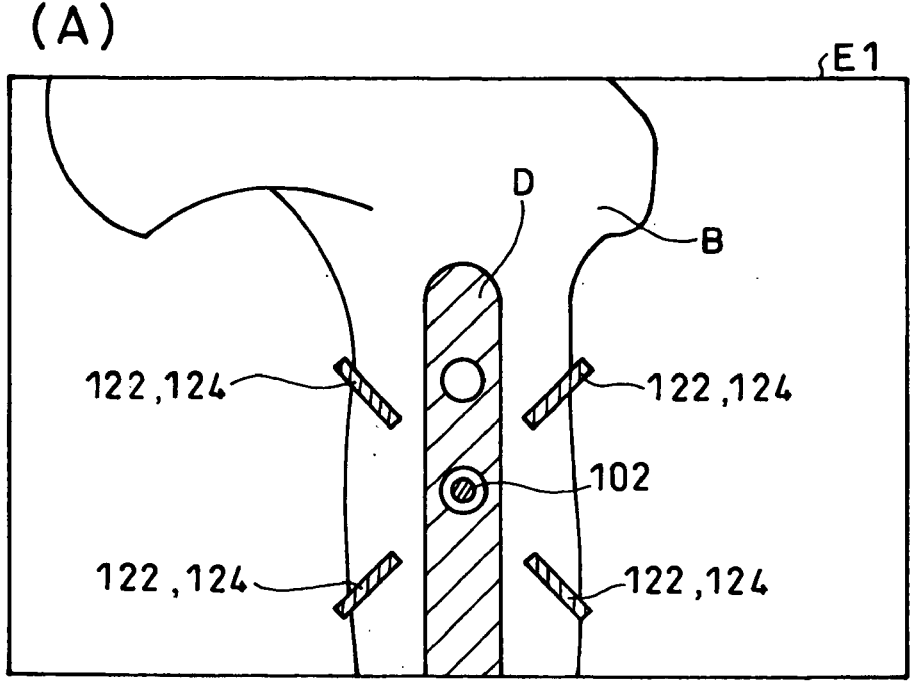
FIGS. 5(A) and 5(B) are diagrams showing images produced by X-rays while the medical drilling machine is being used.
Figure 5:
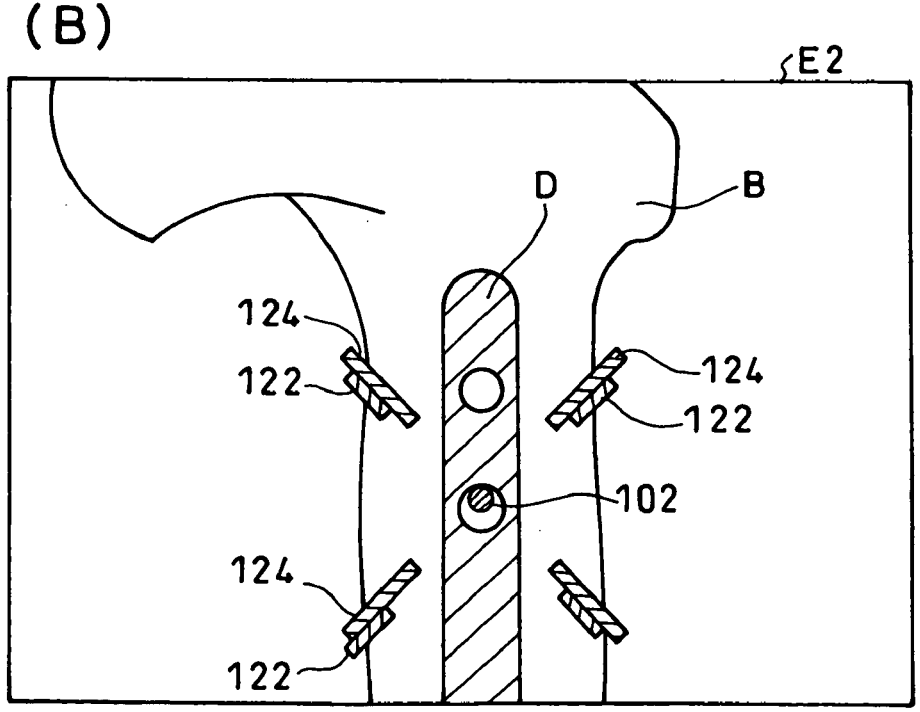

When the doctor inserts the drill machine 100 into the X-ray radiation field, an image E1 as shown in FIG. 5(A) is obtained. This image E1 shows, for example, the bone B, bone-setting material D inserted into the bone, an end surface of the drill bit 102, the first and the second guides 122, 124, et cetera. Here, since the first and the second guides 122, 124 overlap each other, the doctor can judge that the ideal axial line R and the drive axis 106 (or the drill bit 102) axial line P are, in fact, in alignment. Therefore, if the drill bit 102 is advanced straight forward in this position, the bolt hole C will be formed into the bone B exactly as desired.

However, it is possible that the drill 102 will not advance in a straight line. For example, in a case where the axial line P of the drill bit 102 has slanted with respect to the ideal axial line R, an image E2 such as shown in FIG. 5(B) will be obtained.

Figure 6:
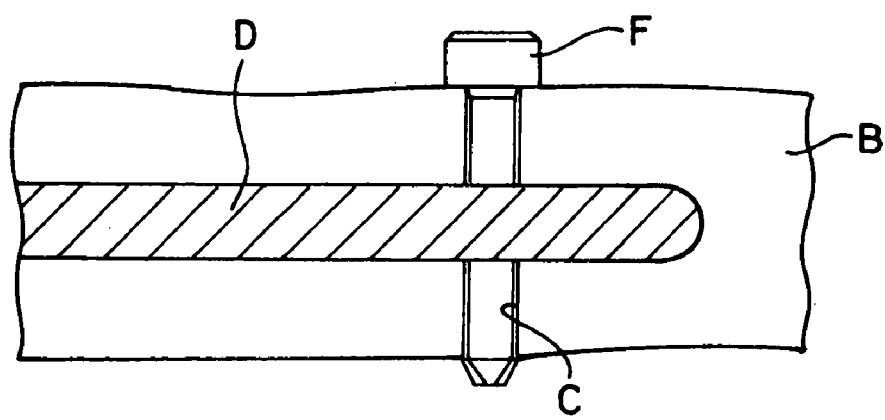
FIG. 6 is a diagram of a bone having been operated on using the medical drilling machine.

In this image E2, the first guide 122 and the second guide 124 are misaligned. Since the first guide and the second guide 124 are shaped differently, the doctor can observe the difference in shape, and can observe the slant direction (including the direction of the misalignment) of the drill bit 102 with respect to the ideal axial line R, based on the relative misalignment of the first guide 122 and the second guide 124. For example, in the image E2, the second guide 124 (which is relatively longer) is displaced above the first guide 122. Therefore, one can judge that the drill bit 102 has slanted upward with respect to the ideal axial line R. As a result, the slanting direction of the drill bit 102 can be immediately recognized and corrected, in order to bore the hole C substantially in line with the direction of the ideal axial line R. As a result, the bone-setting material D and the bolt F inserted into the bolt hole C can be firmly connected, for example, as shown in FIG. 6.

Furthermore, in the present drill machine 100, since the first and second bearings 112, 114 along the axial line P are effectively utilized for accommodating the guides 122, 124 thereinside, the structure becomes simple and manufacturing costs are reduced.

Now, this type of drill machine 100 is held at various angles by the doctor or other user, and it is particularly common for the grip portion 125 to be held horizontally. Therefore, if the machine is not integrally formed as a single unit, or if the weight of the machine is distributed poorly, a large burden is created for doctor.

In the present drill machine 100, in addition to the easy correction of the path traveled by the drill bit 102 by virtue of the guides 122, 124, since the drive motor 116 and the battery 118 are formed as a single unit, external wiring or piping or the like are unnecessary. This facilitates complicated handling of the drill machine 100, and enables better positioning of the drill bit 102.

Figure 7:
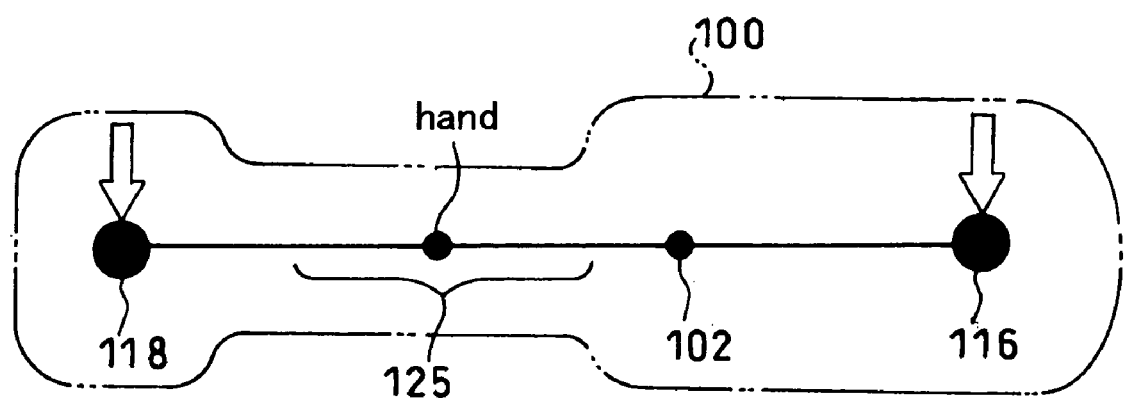
FIG. 7 is a schematic view showing weight distribution in the medical drilling machine.

Additionally, in the case where, for example, the grip portion 125 is held substantially horizontally, the battery 118, the grip portion 125, the drill bit 102 (the drive shaft) and the drive motor 116 are lined up in sequence such that the heavier battery 118 and the drive motor 116 are positioned at either end as shown schematically in FIG. 7. This achieves excellently balanced weight distribution in the machine 100. As a result, the burden borne by the arm of the doctor or other user is diminished.

Note that, the present invention is not restricted to the configuration in which the parts are arranged in the sequence shown in FIG. 7. For example, they may be arranged with the battery 118 first, followed by the grip portion 125, the drive motor 116, and then the drill bit 102, so as to give a heavier sense to both ends of the grip portion 125 to improve the weight distribution (this configuration is recited in claim 5 of the present invention).

Next, explanation is given regarding another example of usage of the drill machine 100.

In general, when forming a relatively long insertion hole in a bone along the axial direction, the drill bit must also be equivalently longer. When the longer drill bit is held in place by the chuck, the tip of the drill bit diverges from the axial center when it rotates, whereby the drill bit is likely to drift from the location where the hole is intended.

Figure 8:
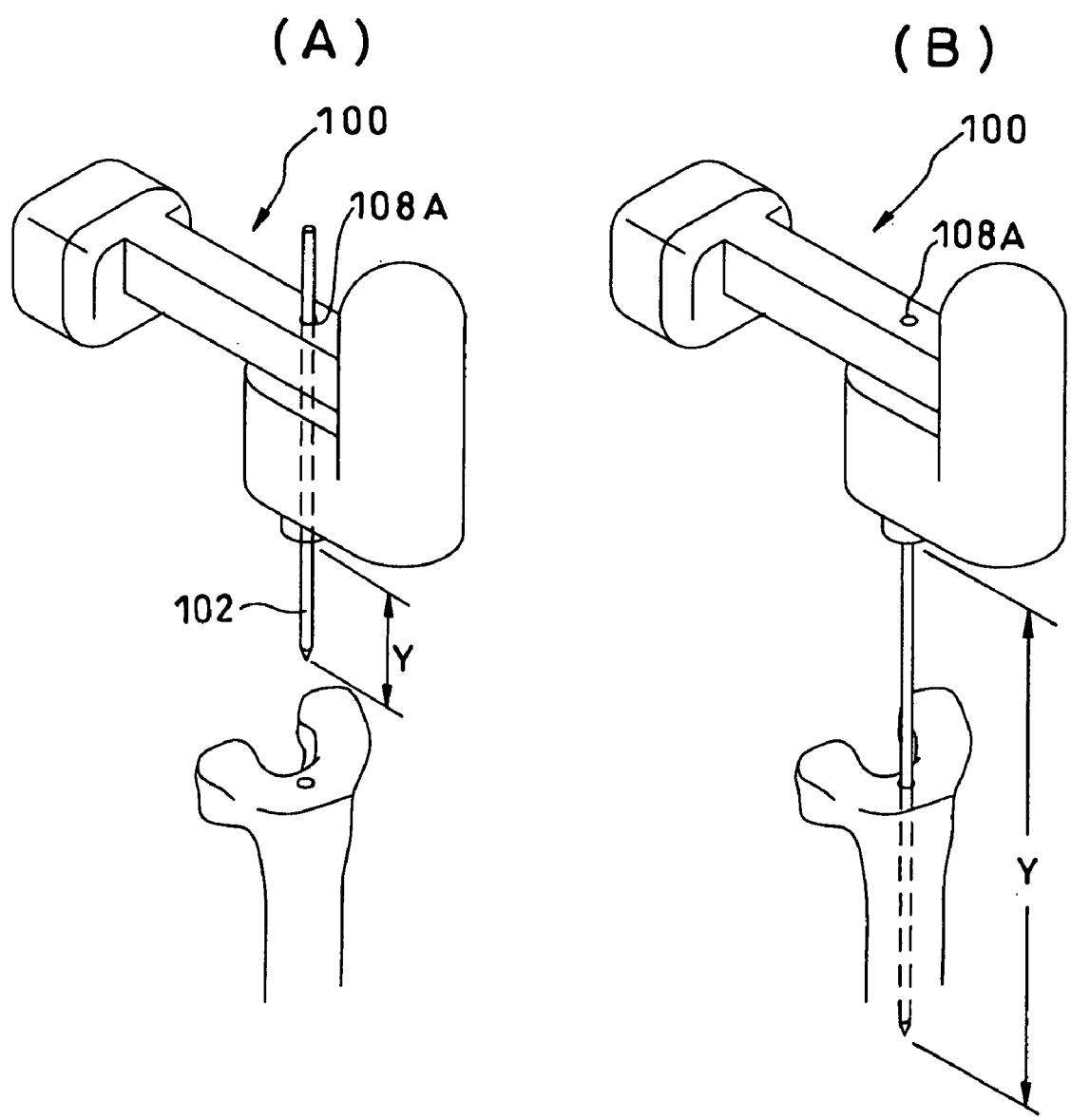
FIGS. 8(A) and (B) are perspective views showing other examples of the medical drilling machine being used.

However, as shown in FIGS. 8(A) and 8(B), in accordance with the drilling machine 100 of the present invention, the back end of the drill bit 102 can be housed into the drive shaft through-hole 106A and the casing through-hole 108A, and furthermore, when the drill bit 102 is particularly long, the drill bit 102 may be passed through these holes 106A, 108A so as to protrude out from the rear side.

As a result, using one long drill bit 102, the tip can be adjusted to an effective length Y as needed, whereby the long hole can be bored easily.

Note that, the present embodiment showed the case where the fist and the second guides 122, 124 are formed in mutually different shapes. Therefore, particularly when the direction of the ideal axial line R and the axial line P of the drive shaft 106 are aligned with each other, the images of the first and the second guides 122, 124 overlap each other. However, the "mutually different shape" of the guides 122, 124 can also include a configuration in which the images of the guides 122, 124 do not overlap each other, and can thus be distinguished from each other at all times.

Figure 9:
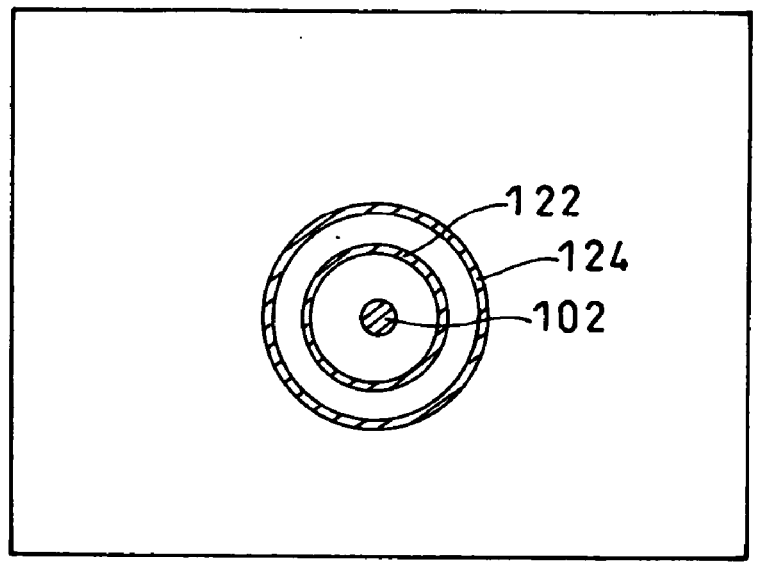
FIG. 9 is a schematic view of another example of guides in the medical drilling machine.
Figure 10:
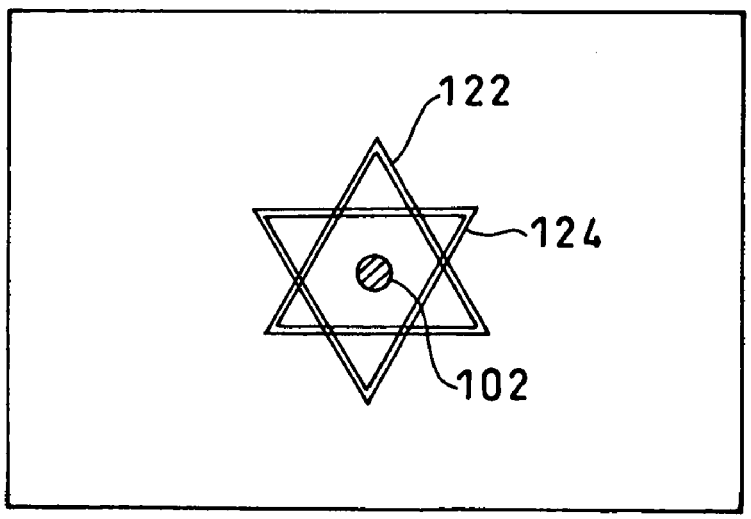
FIG. 10 is a schematic view of yet another example of guides in the medical drilling machine.

For example, as shown in FIG. 9, both the first guide 122 and the second guide 124 are formed as rings. Even if the only difference between the two guides 122, 124 is their relative sizes (i.e., even if they have the same shape), they can be distinguished from one another; therefore, this is included in the concept of the two guides 122, 124 having "mutually different shapes." Furthermore, this also includes a case such as shown in FIG. 10, in which the first and the second guides 122, 124 are formed as equilateral triangles of the same size arranged in different phase positions.

Figure 11:
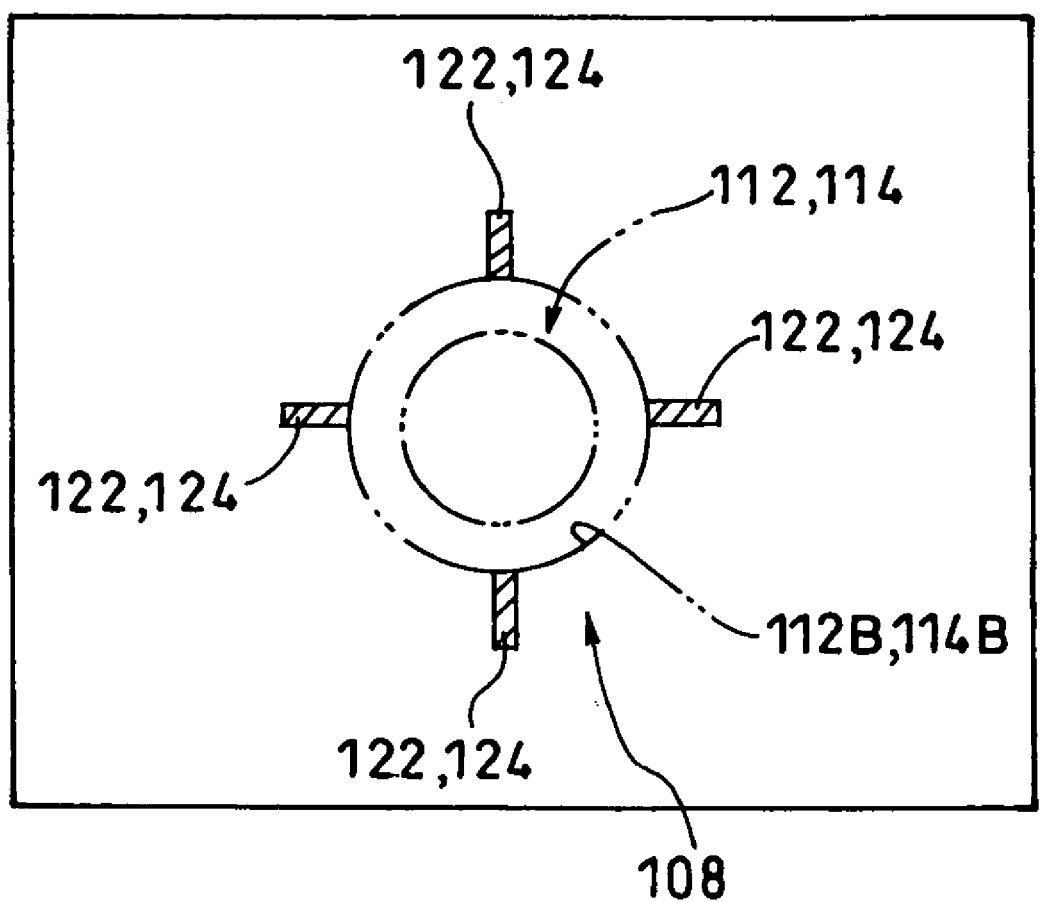
FIG. 11 is a schematic view of yet another example of guides in the medical drilling machine.
Figure 12:
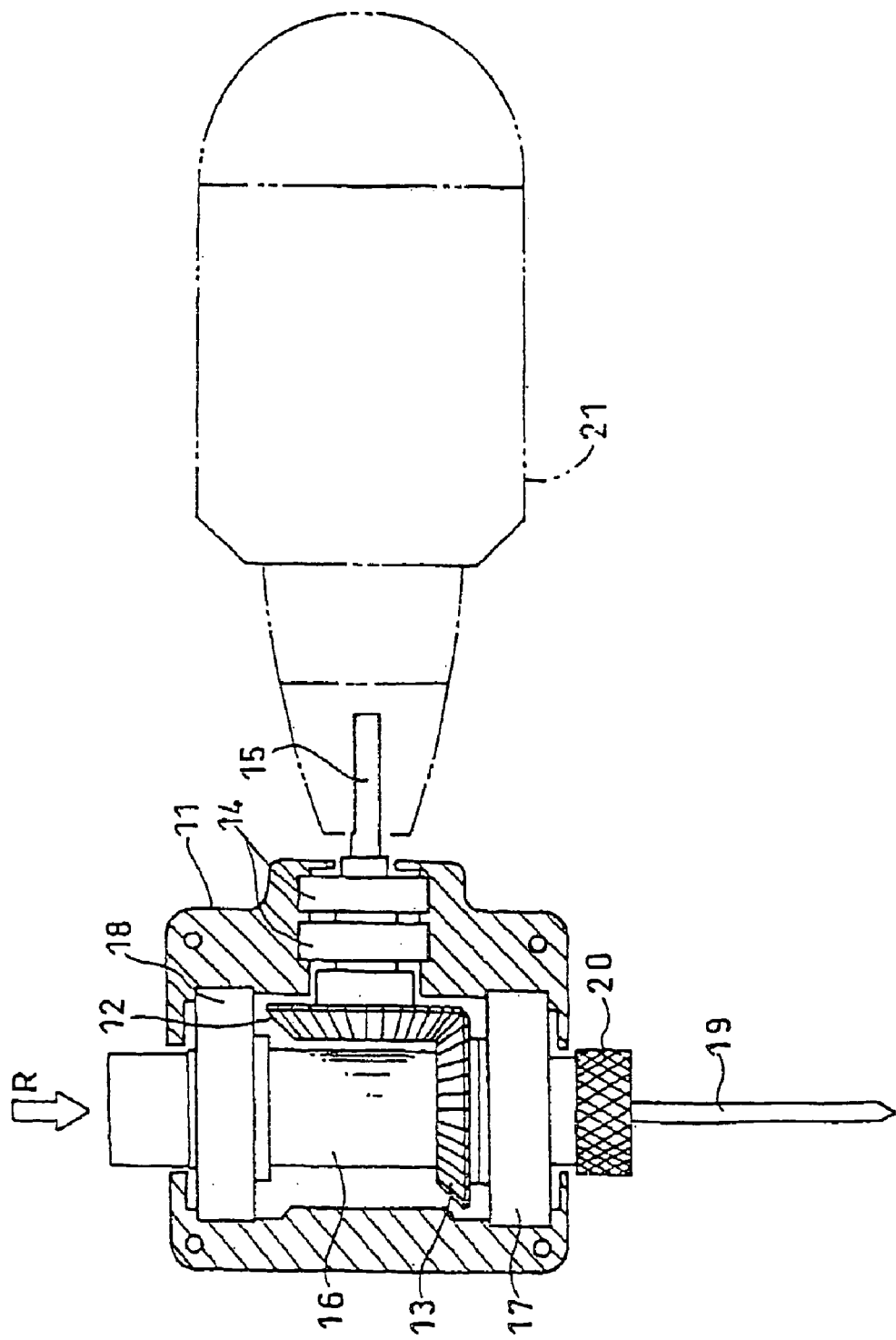
FIG. 12 is an overall view of a conventional medical drill.
Figure 13:
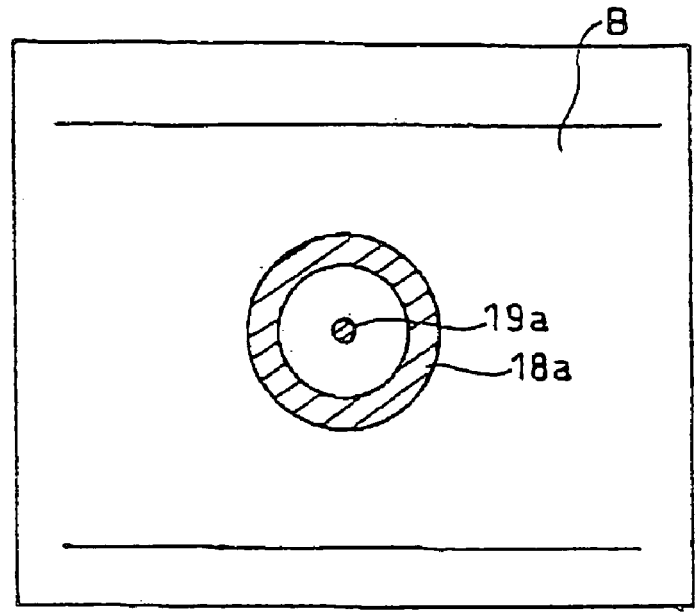
FIG. 13 is a diagram showing an image produced by X-rays while the conventional medical drill machine is being used.
Figure 14:
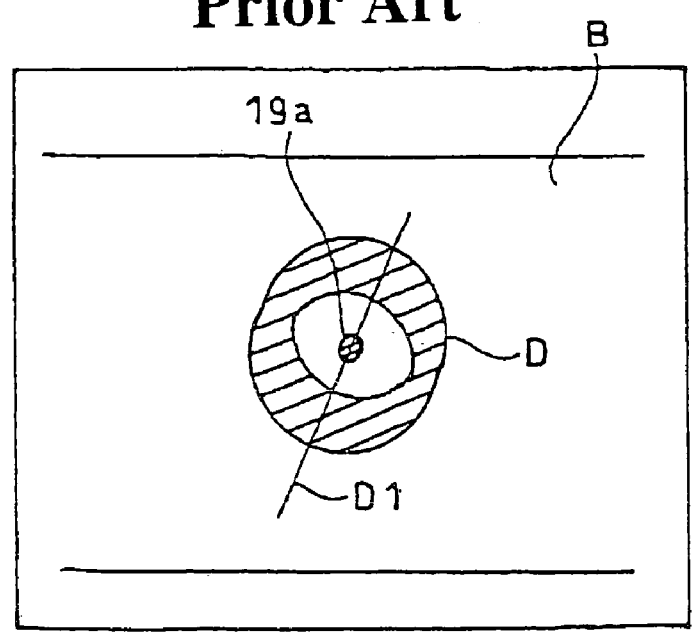
FIG. 14 is a diagram showing another image produced by X-rays while the conventional medical drill machine is being used.
Figure 15:
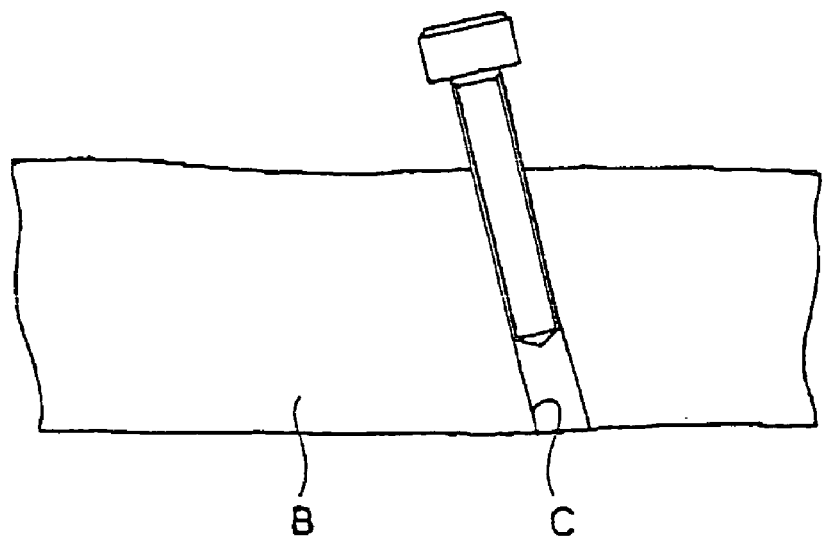
FIG. 15 is a diagram showing an example of a drill hole bored using the conventional medical drilling machine

The present embodiment illustrated the case where the guides 122, 124 are provided inside the bearings 112, 114. However, for example as shown in FIG. 11, the housing portions may be provided to cylinder portions 112B, 114B which hold the bearings 112, 114 in place in the casing 108, and the guides 122, 124 may be inserted into the housing portions. The guides 122, 124 may also be provided to yet another location.

In the foregoing explanation one embodiment was described. However, as long as the essence of the present invention is not departed from, the present invention includes necessary combinations of its various parts, and also includes partial embodiments of the invention. Therefore, the present invention is not limited to the embodiment described above. Moreover, aspects (including functions and shapes) of elements appearing throughout the entire specification are merely examples, and they do not restrict the scope of the present invention.

The present invention facilitates the positioning of the drill bit, and enables accurate boring of the hole.

What is claimed is:

1. A medical drilling machine, comprising:
   a drive shaft held in place in a rotatable fashion, gripping a drill bit by means of a chuck provided to an end of the drive shaft;
   a casing constituted of X-ray transparent material, being capable of housing the drive shaft,
   a force transfer mechanism for transferring rotational force to the drive shaft; and
   a first guide and a second guide constituted of X-ray opaque material are fixed at given distances from each other along an axial direction of the drive shaft inside the casing, wherein
   the first guide and the second guide are arranged coaxially along an axial center of the drive shaft and are formed in mutually different shapes; and
   X-rays are radiated along a direction of an ideal axial line traveled by the drill bit, such that a slant direction of the drill bit with respect to the ideal axial line can be observed from any relative misalignment of, and the mutually different shape of, the first and the second guides.

2. The medical drilling machine according to claim 1, wherein
   the drive shaft is held in a rotatable fashion by means of a first bearing and a second bearing constituted of X-ray transparent material, and predetermined housing portions are formed to non-rotating portions of the first and the second bearings; and
   X-ray opaque material is inserted into the housing portions of the first and the second bearings to provide the first guide in the first bearing, and the second guide in the second bearing.

3. The medical drilling machine according to claim 1, wherein
   the casing is provided with a drive motor for making the drive shaft rotate via the force transfer mechanism, and a battery for the drive motor.

4. The medical drilling machine according to claim 2, wherein
   the casing is provided with a drive motor for making the drive shaft rotate via the force transfer mechanism, and a battery for the drive motor.

5. The medical drilling machine according to claim 3, wherein
   the drive motor is arranged to be displaced from the axial line of the drive shaft, and a motor shaft of the drive motor is arranged in parallel with the axial line;
   a grip portion is provided as an integral part of the casing, on an opposite side of the drive shaft from the side where the drive motor is located; and
   the battery is provided to a grip end side of the grip portion.

6. A medical drilling machine according to claim 3, wherein
   the drive motor is arranged to be displaced from the axial line of the drive shaft, and a motor shaft of the drive motor is arranged in parallel with the axial line;
   a grip portion is provided as an integral part of the casing, on an opposite side of the drive motor from the side where the drive shaft is located; and
   the battery is provided to a grip end side of the grip portion.

7. The medical drilling machine according to claim 1, wherein
- a drive shaft through-hole is provided along the axial line of the drive shaft, and a casing through-hole is provided in the casing along the line of extension of the drive shaft through-hole; and
- a back end of the drill bit held by the drive shaft can be housed into both the drive shaft through-hole and the casing through-hole.

8. The medical drilling machine according to claim 2, wherein
- a drive shaft through-hole is provided along the axial line of the drive shaft, and a casing through-hole is provided in the casing along the line of extension of the drive shaft through-hole; and
- a back end of the drill bit held by the drive shaft can be housed into both the drive shaft through-hole and the casing through-hole.

9. The medical drilling machine according to claim 3, wherein
- a drive shaft through-hole is provided along the axial line of the drive shaft, and a casing through-hole is provided in the casing along the line of extension of the drive shaft through-hole; and
- a back end of the drill bit held by the drive shaft can be housed into both the drive shaft through-hole and the casing through-hole.

10. The medical drilling machine according to claim 4, wherein
- a drive shaft through-hole is provided along the axial line of the drive shaft, and a casing through-hole is provided in the casing along the line of extension of the drive shaft through-hole; and
- a back end of the drill bit held by the drive shaft can be housed into both the drive shaft through-hole and the casing through-hole.

11. The medical drilling machine according to claim 5, wherein
- a drive shaft through-hole is provided along the axial line of the drive shaft, and a casing through-hole is provided in the casing along the line of extension of the drive shaft through-hole; and
- a back end of the drill bit held by the drive shaft can be housed into both the drive shaft through-hole and the casing through-hole.

12. The medical drilling machine according to claim 6, wherein
- a drive shaft through-hole is provided along the axial line of the drive shaft, and a casing through-hole is provided in the casing along the line of extension of the drive shaft through-hole; and
- a back end of the drill bit held by the drive shaft can be housed into both the drive shaft through-hole and the casing through-hole.

* * * * *